United States Patent [19]

Ziegenhorn et al.

[11] 4,229,527
[45] Oct. 21, 1980

[54] PROCESS AND REAGENT FOR THE KINETIC DETERMINATION OF ENZYME SUBSTRATES

[75] Inventors: Joachim Ziegenhorn, Unterpfaffenhofen; August W. Wahlefeld, Weilheim; Alexander Hagen, Tutzing; Wolfgang Grüber, Tutzing-Unterzeismering; Hans U. Bergmeyer, Tutzing, all of Fed. Rep. of Germany

[73] Assignee: Boehringer Mannheim GmbH, Mannheim, Fed. Rep. of Germany

[21] Appl. No.: 954,139

[22] Filed: Oct. 23, 1978

Related U.S. Application Data

[63] Continuation of Ser. No. 751,777, Dec. 16, 1976, abandoned.

[30] Foreign Application Priority Data

Dec. 24, 1975 [DE] Fed. Rep. of Germany ....... 2558536

[51] Int. Cl.² .................... C12Q 1/50; C12Q 1/54; C12Q 1/48; C12Q 1/44
[52] U.S. Cl. .................................. 435/11; 435/14; 435/15; 435/19; 435/25; 435/26; 435/28; 435/810

[58] Field of Search ............... 195/103.5 R, 103.5 C, 195/99, 127; 435/11, 14, 15, 19, 25, 26, 28, 810

[56] References Cited

U.S. PATENT DOCUMENTS

| | | | |
|---|---|---|---|
| 3,862,009 | 1/1975 | Wahlefeld et al. | 195/103.5 R |
| 3,886,045 | 5/1975 | Meittini | 195/103.5 C |
| 3,977,944 | 8/1976 | Muller-Matthesius et al. | 195/103.5 R |
| 3,979,262 | 9/1976 | Hunziker | 195/103.5 R |

OTHER PUBLICATIONS

Segel, *Enzyme Kinetics*, John Wiley & Sons, Inc., N.Y., (1975).
Bergmeyer, "Determination of Enzyme Activities", *Methods of Enzymatic Analysis*, Academic Press, Inc., New York (1974) pp. 121–131.

*Primary Examiner*—Thomas G. Wiseman
*Attorney, Agent, or Firm*—Sprung, Felfe, Horn, Lynch & Kramer

[57] ABSTRACT

Kinetic determination of enzyme substrates by means of coupled reactions comprising selecting the reaction parameters so that the most specific part reaction of a reaction sequence becomes rate-determining for the whole reaction sequence wherein the rate-determining part reaction follows first or pseudo-first order kinetics.

5 Claims, No Drawings

PROCESS AND REAGENT FOR THE KINETIC DETERMINATION OF ENZYME SUBSTRATES

This is a continuation, of application Ser. No. 751,777, filed Dec. 16, 1976, now abandoned.

The present invention relates to a process for the kinetic determination of enzyme substrates by means of coupled reactions and, in addition, relates to a reagent for carrying out this process.

The most commonly used method for enzymatic substrate determination is the so-called end-point method. In this case, the substrate to be determined of an enzymatic reaction is measured by allowing the reaction to proceed to completion, i.e., until all of the substrate has reacted. In the case of numerous conventional end-point methods for the determination of a substrate, especially in automatic analyzers, the time required for each analysis is, at the moment, 10 to 20 minutes. This is unsatisfactory because the time required is too high and optimum utilization of the measuring apparatus and of the automatic analyzers is prevented.

It is known that by use of the kinetic process, in which the substrate concentration is measured by measurement of the rate of the determination reaction, a drastic reduction of the usual analysis times can be achieved. This is, not least, also due to the fact that, in the case of this process, in contradistinction to the end-point method, the determination of sample blanks is generally not necessary.

The theoretical basis for the kinetic substrate determination is described in detail in Anal. Chem., 43, 697 and in Advan. Anal. Chem. Instrum., 7, 141. From these references, it is known that reactions following first and pseudo-first order kinetics are of special importance since the measurement thereof can be followed by use of automated instruments, especially simply according to the so-called "fixed-time" principle.

In the case of the "fixed-time" process, the change of concentration of the substance to be determined or of one of the products resulting therefrom is measured within a fixed period of time. If the determination reaction follows in the selected period of time first or pseudo-first order kinetics, then the following equation applies:

$$c_o = -\frac{\Delta c}{e^{-kt_1} - e^{-kt_2}}$$

In this equation, k is the rate constant of the reaction, $c_o$ is the initial concentration of the substance to be determined and $\Delta c$ is the change in concentration thereof in the time measurement interval $\Delta t = t_2 - t_1$. From this equation, it can be deduced that the measured change of concentration is directly proportional to the initial concentration which is to be determined when k, $t_1$ and $t_2$ are kept constant. These latter conditions can easily be maintained in automatic analyzers, for which reason this process can be used especially advantageously in devices of this type.

It is also already known to select the process conditions so that a reaction of pseudo-zero order kinetics is obtained. However, a quantitative determination is then only possible by way of approximation methods, which frequently make necessary the production of calibration curves.

In the above-mentioned publications and also in other literature references which have hitherto been concerned with kinetic substrate determinations, there is, in the first place, discussed the applicability of the process in one-step reactions. However, such reactions are of only limited importance. In other words, it is frequently necessary to make up the test systems from several part reactions in the interest of adequate specificity and practicability. On the other hand, it is not known how such coupled test systems are to be made up in such a manner that they can be used to determine substrate concentrations on a kinetic basis under routine conditions. Indeed, it has recently been pointed out that coupled reactions make kinetic determination problematical (see Chem. Rundschau, 26, 24/1973) since, for example, a loss of activity of participating enzymes quickly makes the process unusable. Therefore, the view has hitherto been held that a one-step process is to be preferred to the two-step process, and certainly to a multi-step process, precisely in the case of enzyme-kinetic substrate measurements. This explains why, hitherto, coupled test systems, with which substrate concentrations can be determined kinetically under routine conditions, have not proved to be of use in practice.

Therefore, there has been a need for a process for the determination of substrate concentrations by means of coupled reactions on a kinetic basis which can be carried out under routine conditions and in which the part steps of a multi-step test system take place wholly or partly with enzyme catalysis.

The present invention provides such a process for the kinetic determination of an enzyme substrate by means of coupled reactions. In accordance with the invention, the reaction parameters are so selected that the most specific part reaction of a reaction sequence becomes rate-determining for the whole reaction sequence, the rate-determining step following first or pseudo-first order kinetics.

By a coupled reaction, there is to be understood a sequence of at least two part reactions, at least one of which is catalyzed enzymatically, in which the reaction of the substrate and the indicator reaction take place in different reaction steps.

The possibilities of carrying out the most specific part reaction in such a manner that it is rate-determining and follows pseudo-first order kinetics include appropriate selection of the enzymes employed, artificial change of the Michaelis constant of one or more of the enzymes employed, changes of the substrate, appropriate choice of the concentrations of the participating enzymes and reagents, of the temperature and of the pH value and the use of co-factors, accelerators and inhibitors.

Preferably, the less specific part reaction or reactions is or are accelerated by an overdosing of the enzymes which are effective in these part reactions. This embodiment has the additional advantage that a change of activity of this enzyme by storage influences is compensated. In the case of the enzyme of the most specific part reaction, however, a decrease of activity does not play an important part since, in general, the Michaelis constant is hereby certainly not influenced. Naturally, however, it is necessary to prevent a complete loss of the activity of this enzyme, for which purpose conventional methods of enzyme stabilization can be employed, which are well known in the art.

An overdosing is to be understood to mean the use of an amount of enzyme which is at least twice as large and preferably several times larger than the amount of enzyme which would itself be necessary for a rapid course of the reaction. By means of appropriate amounts of the enzymes employed for the part steps, there can certainly, as mentioned above, be obtained considerable variations of the rates of the individual part reactions so that, in a relatively simple manner, those reactions can be made rate-determining which show the most specific course.

The nature of the enzymes employed can be changed by selecting an enzyme of definite origin, depending upon the desired Michaelis constant. Thus, enzymes of different origin which catalyze the same reaction, can have different Michaelis constants, depending upon whether they are obtained, for example, form microorganisms or from mammalian liver.

An artificial change of the Michaelis constant can be achieved, for example, by changing the metal atom in the active center of the enzyme. Another possibility is the partial splitting of the enzyme, either by dissociation into its sub-units, when the enzyme consists of these, or by proteolytic splitting off of a part of the peptide chain. Another possibility in a chemical modification of the active center. This can take place, for example, by changing individual reactive groups of amino acids of the center, such as the oxidation of an SH group or the like. Further possibilities for the artificial change of the Michaelis constant include a conformation change of the enzyme by the addition of an allosteric effector, by the addition of certain ions, by appropriate selection of the nature of the buffer, by adjustment of particular salt concentrations in the solution and the like.

The substrate itself can be changed by complexing by the addition of appropriate complex formers, by micelle formation, for example by the addition of a detergent, or the like.

The pH value can also be used to influence the rate of reaction in the manner according to the present invention. Thus, the enzyme of that part reaction which is to be made rate-determining can be used at a non-optimum pH value, which leads to an increase of the Michaelis constant of this enzyme. Furthermore, the temperature dependence of enzymes can also be utilized, although this is not preferred since the generally desired objective is to make uniform the temperature of enzymatic determination reactions.

Further means for influencing the rate of the part reactions in the process according to the present invention include the addition of reaction components and reaction products which truly or apparently change the Michaelis constant of an enzyme. In the same way, inhibitors can also be employed, this latter method being known, for example, from German Patent Specification No. 2,349,819. Finally, the rate of a non-enzymatic part reaction can be influenced by the addition of a catalyst or of an inhibitor.

By the most specific part reaction of the reaction sequence, there is to be understood that part reaction which exhibits the greatest specificity with regard to the substance to be determined and, furthermore, can be made rate-determining by appropriate choice of the reaction parameters. This part reaction can be enzymatically catalyzed but this is not essential. An example of a non-enzymatic reaction of pseudo-first order with a very high specificity is the mutarotation between alpha- and beta-glucose. When the most specific part reaction itself cannot be made rate-determining, for example, in the case of too low a true or apparent Michaelis constant of the enzyme, then the next most specific part reaction which can be made rate-determining counts as the most specific part reaction within the meaning of the present invention.

A further important feature of the present invention is that the rate-determining step must be carried out in such a manner that it follows first or pseudo-first order kinetics. If the most specific part reaction which is made rate-determining follows, in any case first or pseudo-first order kinetics, then special measures in this regard are not necessary. However, it is different in the case of reactions of the second or higher order: in this case, a pseudo-first order must be brought about. This can be achieved when the concentration of the second or further reaction components, which is not the substrate to be determined or a product thereof, is kept practically constant by appropriate dosing during the reaction, i.e., is used in excess. Furthermore, in the case of an enzymatic reaction, the Michaelis constant is selected to be so high that it is large in comparison with the upper limit of the substrate concentration coming into consideration in the test.

The present invention also provides a reagent for the kinetic determination of enzyme substrates by means of coupled enzymatic reactions, this reagent comprising such enzymes and reaction components and in such amounts that the most specific part reaction of the reaction sequence taking place upon the addition of the substrate to an aqueous solution of the reagent is rate-determining for the whole of the reaction sequence and follows first or pseudo-first order kinetics.

According to a preferred embodiment of the reagent of the present invention, it contains an overdose of the enzyme or enzymes of the less specific part reaction or reactions.

The present invention enables enzyme-kinetic substrates measurements to be carried out in coupled test systems and thus considerably reduces the time necessary for carrying out such determinations. At the same time, there is achieved a substantial independence from the activity of the participating enzymes so that the precision of the process is then also fully obtained when, due to storage, a substantial loss of activity has already taken place in the case of the participating enzymes. Furthermore, the present invention enables such multi-step enzyme-kinetic substrate measurements to be carried out in all conventional automatic analyzers, so that, on the basis of the teachings of the present invention, it is possible, without difficulty, to adapt the quantitative compositions of the reagents to any desired automatic analyzers.

The following Examples are given for the purpose of illustrating the present invention:

EXAMPLE 1

Blood Sugar Determination By the GOD/PAP method

The determination takes place according to the following equation:

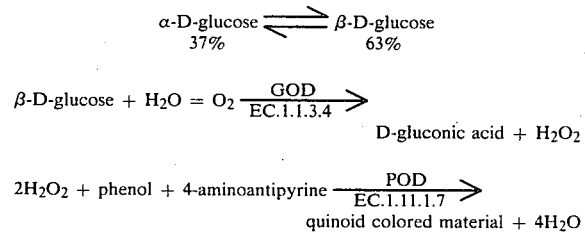

The enzyme peroxidase (POD) is overdosed to such an extent that the mutarotation between alpha- and beta-glucose, which follows strictly pseudo-first order kinetics, or the glucose oxidase (GOD) reaction, which also follows pseudo-first order kinetics because of the high $K_M$ with regard to glucose, becomes the rate-determining step. This is achieved by means of a reagent having the following composition:

80–120 mM phosphate buffer, pH 7.0
0.8 U/ml. or more of POD
12 U/ml or more of GOD
0.6–1.80 mM 4-aminoantipyrine
3.0–73.5 mM phenol.

The above reagent is especially suitable for carrying out the process with a Centrifugal-fast analyzer. The first reading is made about 35 seconds after mixing the reagent with the sample to be investigated and the second reading is made 1.5 to 3.5 minutes later. With 500 to 600 μl. of reaction mixture and 5 to 20 μl. of sample, there can be determined up to 1000 mg. of blood sugar/100 ml.

EXAMPLE 2

Triglyceride Determination

The triglycerides are split enzymatically into glycerol and fatty acids. The determination of the glycerol takes place according to the following reactions:

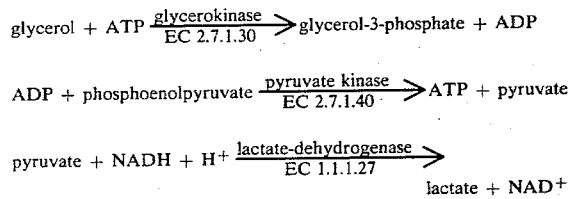

The process is carried out kinetically with the following reagents:

Reagent 1

45–55 mMol/l. phosphate buffer, pH 7.0
4.6–3.1 mMol/l. magnesium sulphate
300–400 μmol/l. sodium dodecyl sulphate
2.3–3.5 mMol/l. ATP
280–420 μmol/l. phosphoenol pyruvate
120–230 μmol/l. NADH
$7.7 \times 10^4$ U/l. or more of lipase
$5.8 \times 10^2$ U/l. or more of esterase
$9.6 \times 10^2$ U/l. or more of pyruvate kinase
$5.3 \times 10^3$ U/l. or more of lactate dehydrogenase

Reagent 2

$2.9 \times 10^3$ U/l. or more of glycerokinase

The reaction is measured with a Centrifugal fast analyzer at 340 nm and 25° C. By increasing the ATP concentration in the test, the Michaelis constant of the pyruvate kinase is apparently increased to such a height that it is large in comparison with the glycerol upper limit in the test. The other enzymes are overdosed. In this manner, the pyruvate kinase reaction becomes rate-determining and the glycerol concentration can be determined from the reaction velocity.

For carrying out the determination, 10 μl. of a serum sample to be investigated are mixed with 30–50 μl. of physiological sodium chloride solution and 500–600 μl. of the reagent which does not contain the glycerokinase and left to stand for 10 minutes. The glycerokinase is then added thereto and after 50 seconds the first reading is made and after 150–200 seconds, the second reading is made.

The method covers a concentration range of 500 to 9000 mg. triglyceride per liter.

Regression comparison $y = 0.99 \times + 0.51$
Correlation coefficient $r = 0.999$

EXAMPLE 3

Determination of Glycerol

The reaction is carried out kinetically with the following reagents:

Reagent 1

45–55 mMol/l. phosphate buffer, pH 7.0
4.6–3.1 mMol/l. magnesium sulfate
300–400 μmol/l. sodium dodecyl sulfate
2.3–3.5 mMol/l. ATP
280–420 μmol/l. phosphoenol pyruvate
120–230 μmol/l. NADH
$9.6 \times 10^2$ U/l. or more of pyruvate kinase
$5.3 \times 10^3$ U/l. or more of lactate dehydrogenase

Reagent 2

$2.9 \times 10^3$ U/l. or more of glycerokinase

The reaction is measured with a Centrifugal fast analyzer at 340 nm and 25° C.

By increasing the ATP concentration in the test, the Michaelis constant of the pyruvate kinase is apparently increased to such a height that it is large enough in comparison with the glycerol upper limit in the test. The other enzymes are overdosed. In this way, the pyruvate kinase reaction becomes rate-determining and the glycerol concentration can be determined from the reaction velocity.

For carrying out the determination, 100 μl. of a serum sample to be investigated are mixed with 100 μl. of physiological sodium chloride solution and 500–600 μl. of the reagent which does not contain glycerokinase. The glycerokinase is then added and after 50 seconds the first reading is made and after 150–200 seconds, the second reading is made.

The method covers a concentration range of 5 to 90 mg. glycerol per liter.

EXAMPLE 4

Total Cholesterol

The determination takes place according to the following equation:

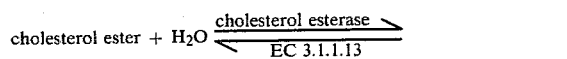
cholesterol + fatty acid

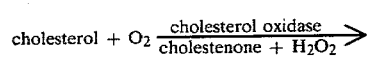

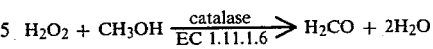

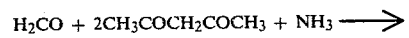

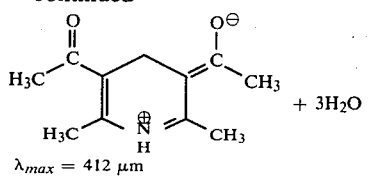

$\lambda_{max} = 412 \mu m$

By overdosing the enzymes cholesterol esterase and cholesterol oxidase, the color reaction which follows pseudo-first order kinetics becomes rate-determining. The process can be carried out, for example, on an Eppendorf 5032 automatic device with the following reagent:

0.45–0.75 mol/l. ammonium phosphate buffer, pH 7.0
1.36–2.04 mol/l. methanol
16–24 mMol/l. acetylacetone
0.79–1.19 g./l. hydroxypolyethoxydodecane
500 kU/l. or more of catalase
20 U/l. or more of cholesterol esterase
20 U/l. or more of cholesterol oxidase A blank reagent made up in the same manner does not contain cholesterol oxidase.

For carrying out the determination with an Eppendorf 5032 automatic apparatus, 0.01 ml. of the sample to be investigated is mixed with 1.0 ml. of the reagent and incubated at 37° C. for 20 minutes, the extinction then being read off at Hg 405 nm.

The same procedure is carried out with a blank batch of the same composition except that it does not contain cholesterol oxidase. The amount of cholesterol is calculated from the extinction difference between the sample batch and the blank batch.

Regression line $y = 0.98 \times + 1.98$
Correlation coefficient $r = 0.997$.

It will be understood that the specification and examples are illustrative but not limitative of the present invention and that other embodiments within the spirit and scope of the invention will suggest themselves to those skilled in the art.

What is claimed is:

1. Process for the kinetic determination of an enzyme substrate which process comprises subjecting the substrate to at least two enzymatic part reactions in a sequence of reactions to yield an indicating substance, selecting the part reaction which exhibits the greatest specificity with regard to the starting substance of the reaction, overdosing the enzyme or enzymes of the other part reaction or reactions by an amount at least twice as large as the amount normally necessary for the reaction so that said most specific part reaction becomes rate-determining and follows first or pseudo first order kinetics, and measuring a change in the indicating substance during a preselected time interval.

2. Process as claimed in claim 1 wherein there is only one other part reaction and the said most specific part reaction is rate-determining by overdosing the enzyme of said other part reaction.

3. Reagent kit for the determination of triglycerides, comprising Reagents 1 and 2 wherein Reagent 1 is composed of
   45 to 55 mMol/l. phosphate buffer (pH 7.0),
   4.6 to 3.1 mMol/l. magnesium sulphate,
   300 to 400 $\mu$mol/l. sodium dodecyl sulphate,
   2.3 to 3.5 mMol/l. adenosine triphosphate,
   280 to 420 $\mu$mol/l. phosphoenol pyruvate,
   120 to 230 $\mu$mol/l. nicotinamide-adenine dinucleotide (reduced),
   $7.7 \times 10^4$ U/l. or more of lipase,
   $5.8 \times 10^2$ U/l. or more of esterase,
   $9.6 \times 10^2$ U/l. or more of pyruvate kinase, and
   $5.3 \times 10^3$ U/l. or more of lactate dehydrogenase,
and Reagent 2 is composed of
   $2.9 \times 10^3$ U/l. or more of glycerokinase.

4. Reagent kit for the determination of glycerol, comprising Reagents 1 and 2 wherein Reagent 1 is composed of
   45 to 55 mMol/l. phosphate buffer (pH 7.0),
   4.6 to 3.1 mMol/l. magnesium sulphate,
   300 to 400 $\mu$mol/l. sodium dodecyl sulphate,
   2.3 to 3.5 mMol/l. adenosine triphosphate,
   280 to 420 $\mu$mol/l. phosphoenol pyruvate,
   120 to 230 $\mu$mol/l. nicotinamide-adenine dinucleotide (reduced),
   $9.6 \times 10^2$ U/l. or more of pyruvate kinase,
   $5.3 \times 10^3$ U/l. or more of lactate dehydrogenase,
and Reagent 2 is composed of
   $2.9 \times 10^3$ U/l. or more of glycerokinase.

5. Reagent for the determination of total cholesterol, comprising
   0.45 to 0.75 mol/l. ammonium phosphate buffer (pH 7.0),
   1.36 to 2.04 mol/l. methanol,
   16 to 24 mMol/l. acetylacetone,
   0.79 to 1.19 g./l. hydroxypolyethoxydodecane,
   500 kU/l. or more of catalase,
   20 U/l. or more of cholesterol esterase, and
   20 U/l. or more of cholesterol oxidase.

* * * * *